United States Patent [19]

Corrado

[11] Patent Number: 4,822,474
[45] Date of Patent: Apr. 18, 1989

[54] RESIDUAL ANALYZER ASSEMBLY

[75] Inventor: Daniel R. Corrado, Berkeley Heights, N.J.

[73] Assignee: Pennwalt Corporation, Philadelphia, Pa.

[21] Appl. No.: 44,876

[22] Filed: Apr. 30, 1987

[51] Int. Cl.$^4$ .......................................... G01N 27/46
[52] U.S. Cl. .................................... 204/402; 73/863; 73/863.03; 204/1 T; 204/400; 204/409; 204/412; 204/435
[58] Field of Search ............... 204/1 B, 1 T, 400, 412, 204/435, 402, 409; 73/863, 863.01, 863.02, 863.03

[56] References Cited

U.S. PATENT DOCUMENTS

| | | | |
|---|---|---|---|
| 2,288,180 | 6/1942 | Brengman et al. | 204/435 |
| 2,414,411 | 1/1947 | Marks | 204/402 |
| 2,760,922 | 8/1956 | Williams | 204/435 |
| 3,272,725 | 9/1966 | Garst | 204/1 |
| 3,275,541 | 9/1966 | Strong | 204/402 |
| 3,328,277 | 6/1967 | Solomons et al. | 204/195 |
| 3,380,905 | 4/1968 | Clark, Jr. | 204/195 |
| 3,448,031 | 6/1969 | Robinson | 204/195 |
| 3,454,485 | 7/1969 | Hauk et al. | 204/195 |
| 3,505,195 | 4/1970 | Nielsen et al. | 204/195 |
| 3,518,179 | 6/1970 | Bleak et al. | 204/195 |
| 3,539,455 | 11/1970 | Clark, Jr. | 204/1 |
| 3,542,662 | 11/1970 | Hicks et al. | 204/195 |
| 3,840,438 | 10/1974 | Ast et al. | 204/402 |
| 3,956,094 | 5/1976 | Capuano | 204/402 |
| 4,003,705 | 1/1977 | Buzza et al. | |
| 4,059,406 | 11/1977 | Fleet. | |
| 4,076,596 | 2/1978 | Connery et al. | |
| 4,129,479 | 1/1975 | Morrow. | |
| 4,145,272 | 3/1979 | Nakamura et al. | 204/195 |
| 4,168,220 | 9/1979 | McAdam et al. | |
| 4,182,666 | 1/1980 | Dickinson et al. | 204/195 |
| 4,187,162 | 2/1980 | Dageforde | 204/195 |
| 4,197,853 | 4/1980 | Parker. | |
| 4,256,832 | 3/1981 | Findl et al. | |
| 4,388,166 | 6/1983 | Suzuki et al. | |
| 4,459,180 | 7/1984 | Fogel. | |
| 4,581,121 | 4/1986 | Dailey et al. | |
| 4,605,473 | 8/1986 | Dewald. | |
| 4,627,893 | 12/1986 | Cormeier et al. | 204/1 T |

OTHER PUBLICATIONS

Excerpts from "Electrochemical Methods of Process Analysis" published by the Instrument Society of America, Pittsburgh, PA., 1972.

Primary Examiner—T. Tung
Attorney, Agent, or Firm—Seidel, Gonda, Lavorgna & Monaco

[57] ABSTRACT

A residual analyzer assembly including an analyzer probe, typically of the amperometric type having a stable zero calibration, and a working fluid sampler system having means for backflushing the flow so as to periodically cleanse the system. The residual analyzer probe having two bare electrodes operating as a working electrode and a counter electrode. The working electrode being formed in a double spiral helix with the counter electrode being formed in an outer peripheral ring closely adjacent the working electrode. The probe also including a third electrode within an electrolytic solution and positioned behind a membrane located directly behind the working electrode. The three electrode system operated utilizing a potentiostat type circuit. The working fluid sampler system adapted to sample a portion of the working fluid flow and maintain a constant pressure into a flow block. A controlled amount of reagent being added for proper residual analyzation of the sample. The sample flow being directed into an impeller chamber which provides a constant flow velocity directly adjacent the exposed electrodes of the analyzer probe. A backflush mechanism is also provided to cleanse the internal flow passageways of the system on a periodic basis.

20 Claims, 9 Drawing Sheets

RESIDUAL ANALYZER ASSEMBLY

BACKGROUND OF THE INVENTION

The present invention relates to the analyzation and/or measurement of residual amounts of specific chemical species within a working fluid system. Residual analyzers are typically adapted to measure such chemicals as free chlorine, total chlorine, potassium permanganate or chlorine dioxide within a working fluid and may be applied to such commercial applications as drinking water, waste water, and reactor cooling water. The present invention relates to both a residual analyzer type probe and a working fluid sampler system.

A number of analytical methods may be employed for the determination of specific chemical species within a working fluid. Three of these analytical methods include amperometry, colorimetry and potentiometry. Each of these methods has its limitations and advantages for specific applications. The typical commercial applications involving drinking water and the like often utilize amperometry or potentiometry.

A typical amperometric type probe includes two electrodes having an applied potential across the electrodes. Under ideal conditions, the current produced within the probe is proportional to the concentration of the chemical species that is oxidized and reduced at the electrodes. Therefore, zero concentration of the species within the working fluid should result in no current being produced. In actual use, however, variations in conductivity, pH, temperature, electropotential, interfering substances and electrode and flow fouling may cause significant errors, especially at low residuals (typically below 0.1 mg/l). Liquid or gas reagents are often utilized in such low residual applications for conditioning the working fluid. Means for temperature compensation and the use of applied potentials are also known methods of minimizing the errors associated with this type analyzation. However, a probe utilizing these various means of compensation for the changing characteristics of the working fluid will still require periodic zero calibration for proper continuous operation.

A more recent approach in commercial amperometric type probes includes the utilization of a membrane to isolate the electrodes from the working fluid. The membrane is positioned between the fluid and the electrodes and protects the electrodes from ionized substances while maintaining a stable electrochemical condition at the electrodes. This type structure typically results in a near true and stable zero calibration. However, due to the reduced sensitivity created by the membrane, varying diffusion rates for different species through the membrane and frequent membrane fouling, this type structure is often considered inadequate for the analyzation of reactor cooling water and waste water.

Sensitivity of the probe used in making the residual measurements is a significant factor in the commercial applicability of a probe assembly to a specific working fluid. Other operational factors, however, must also be considered in evaluating the overall cost of a continuous system. A typical residual analyzer probe which includes a membrane, although inaccurate in cooling water and waste water applications, often reduces operating costs since reagents are not required to condition the working fluid. Reagents are often required for accurate operation of a probe having exposed electrodes without membrane protection. Additionally, reagents are utilized with non-membrane type probes to maintain electrode cleanliness during its continuous operation. The amount of reagents required as well as their effect on the working fluid are often significant considerations in many commercial applications.

BRIEF SUMMARY OF THE INVENTION

The present invention relates to both a residual analyzer probe and a working fluid sampler system which combine to form a complete analyzer assembly. The probe and sampler system are contemplated to function either together, as a complete residual analyzer assembly, or separately with each portion of the invention having its own specific advantages and applications.

The probe contemplated as part of the present invention utilizes bare or exposed working electrodes so as to provide a high level of sensitivity. The contemplated probe also provides means for compensating for variations in the operation characteristics of a working fluid so as to operate at a near true zero reading and maintain a stable zero calibration.

An embodiment of the probe portion of the invention comprises three electrodes including a double spiral wound working electrode, preferably made of a platinum material, a ring or circular shaped counter electrode surrounding the working electrode, preferably also made of platinum, and a reference electrode positioned behind a membrane within an electrolytic fluid in an internal chamber of the probe body. The working and counter electrodes are located in close proximity to one another to minimize ohmic drop. The reference electrode is preferably composed of a coiled silver wire and is maintained within a potassium chloride solution. The membrane is, preferably, made of a hydrophilic polypropylene material and is used to form a reference junction between the working fluid and the reference electrode within the electrolytic solution. The membrane is located directly behind the working electrode so as to sense the potential of the working electrode while the double spiral formation protects the membrane. This type structure will permit the use of grit for cleaning the operational surfaces of the exposed electrodes without substantial damage to the thin membrane material.

The probe as described above is contemplated to be operated utilizing a potentiostat type circuit. This type circuitry has been employed in a variety of electrochemical measurements and laboratory instrumentation and is adaptable to a variety of electrode configurations. The potentiostat circuitry in the present invention will, preferably, maintain a potential between the working and reference electrodes while allowing current to flow only between the counter and working electrodes. The operation of such potentiostat circuits is outlined in "Electrochemical Methods of Process Analysis" published by the Instrument Society of America, Pittsburgh, Pa., 1972, which is herein incorporated by reference. This circuitry is also applicable to probes having two, three or more electrodes in various combinations. The potentiostat arrangement as contemplated by the present invention permits virtually zero current to flow through the reference electrode; thus, rendering a major portion of the element resistance and the impedances between the counter and reference electrodes insignificant. The impedance between the membrane and working electrode may be significant in this type structure, however, this impedance is minimized by the placement of the membrane directly behind the working electrode.

Another feature contemplated for use within the probe portion of the present invention includes the use of a replaceable cap to form the end face of the probe, retain the working and counter electrodes, as well as fix the membrane in its close operational relationship with the electrodes. This cap, preferably, may be unscrewed from the probe body and replaced or cleaned without requiring substantial disassembly of the probe.

The working fluid sampler system portion of the present invention is preferably designed to withdraw a continuous sample of the working fluid flow and direct this sample towards the probe for analyzation while minimizing the amount of reagent required for proper analyzation. The sampler system may also include an automatic backflush mechanism for cleaning the flow passageways and internal structures of the system. A rotating impeller is also provided to maintain a constant sample velocity and may be adapted to direct a continuous flow of a grit material within the impeller chamber to clean the electrodes to insure proper operation and results.

The backflush mechanism of the sampler system is intended to eliminate buildup of materials within the system which may impair operation due to the reduction in the sample flow through the unit. Also, a build up of organic matter in certain applications within the passageways of the system could cause a residual demand and reduce the accuracy of the analyzer probe measurement or completely block flow into the sampler system. The backflush mechanism periodically energizes to reverse the flow through the system to clean the orifices and passageways through which the flow travels and to remove these materials from the system.

The probe contemplated by the present invention provides an accurate means for proper analyzation of a number of type working fluids and compensates for variations in fluid characteristics. The working fluid sampler system contemplated by the present invention limits the amount of reagents required for proper operation of an amperometric type probe and provides a periodic cleansing of the system which may be automatically energized. The combination of the probe and the sample system provides a residual analyzer assembly which substantially reduces operational costs while providing the desired accuracy even at low residual concentration and considering variations in flow charateristics.

Further advantages of the invention will become apparent by providing a detailed description of the preferred embodiment. For the purpose of illustrating the invention, there is shown in the drawings a form which is presently preferred; it being understood, however, that this invention is not limited to precise arrangements and instrumentalities shown.

DETAILED DESCRIPTION OF THE DRAWINGS

Figure 1:
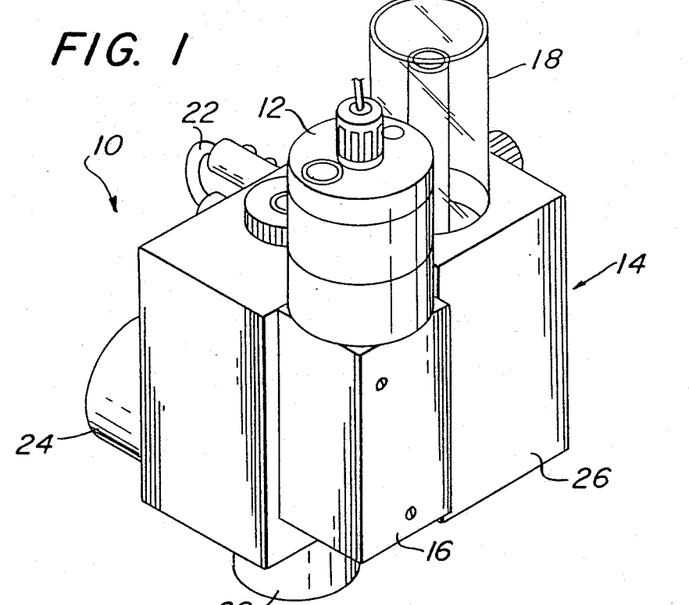
FIG. 1 is an isometric view of a residual analyzer assembly as contemplated by the present invention.

In the drawings, where like numerals indicate like elements, there is shown a residual analyzer assembly 10 as contemplated by the present invention. FIG. 1 illustrates the assembly 10 including a probe portion 12 and a working fluid sampler system 14. The working fluid sampler system includes a probe block 16 which supports the probe 12 and a flow block 26 which defines the flow passageways of the sampler system 14.

The working fluid sampler system 14 of the invention will be described first as including any type probe 12. The probe 12 as contemplated by the invention will be described in detail later. However, in the preferred embodiment of the working fluid sampler system 14 of the present invention an amperometric type probe 12 utilizing bare or exposed electrodes is contemplated. Also, the probe 12 of the invention is not limited strictly to use with the working fluid sampler system 14 as contemplated.

Figure 2:
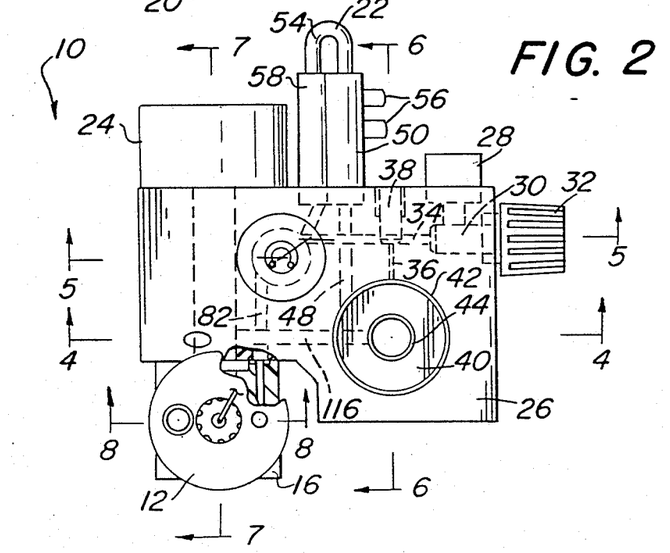
FIG. 2 is a top plan view of the residual analyzer assembly shown in FIG. 1.

FIG. 2 shows a top plan view of the assembly 10 including the probe 12 and illustrating the internal passageways of the working fluid sampler system 14. The sampler system 14, as shown, includes a constant level box 18, a self-cleaning backflush mechanism 20, an adjustable flow delay line 22 and an impeller mechanism 24. All of these structures are supported on or maintained within the flow block 26. The various internal passageways direct a sample of the flow through the system 14 for analyzation and then exhausts the flow back into the working fluid flowpath. The flow block 26 will be described in various sections so as to understand the operational characteristics of the system 14.

Figure 10:
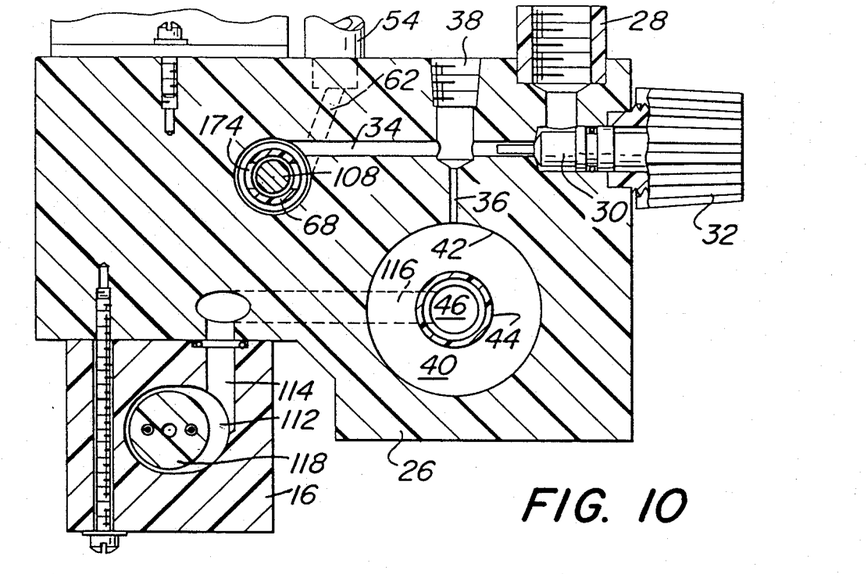
FIG. 10 is a cross-sectional view of the working fluid sample system, as contemplated by the present invention, taken along line 10—10 in FIG. 6.

As shown in FIGS. 2 and 10, the flow inlet 28 is positioned on the rear of the flow block 26. Inlet 28 is adapted to receive a flow line (not shown) and direct the full flow through the block 26 into the constant level box 18. The flow line may include a fitting (not shown) supported on the block 26 by internal threads. Valve means 30 is provided to control the flow rate entering the flow block 26 at inlet 28. Valve means 30 as illustrated in FIG. 10 includes an adjustment knob 32 which is preferably attached to a needle type valve retained within a first passageway 34 (See also FIG. 5).

The flow entering inlet 28 and passing through first passageway 34 is then directed via a second passageway 36 into the constant level box 18 at its base. Second passageway 36 is provided within the flow block 26 via aperture 38. Aperture 38 is required to form the internal intersection of passageway 36 with first passageway 34 within the solid flow block 26. Normally, aperture 38 is plugged after assembly at the rear of flow block 26 to prevent the flow from exhausting out of the flow block 26. First passageway 34 extends beyond its intersection with the second passageway 36 and terminates adjacent the internal bore supporting the backflush mechanism 20 (See FIG. 5).

Figure 3:
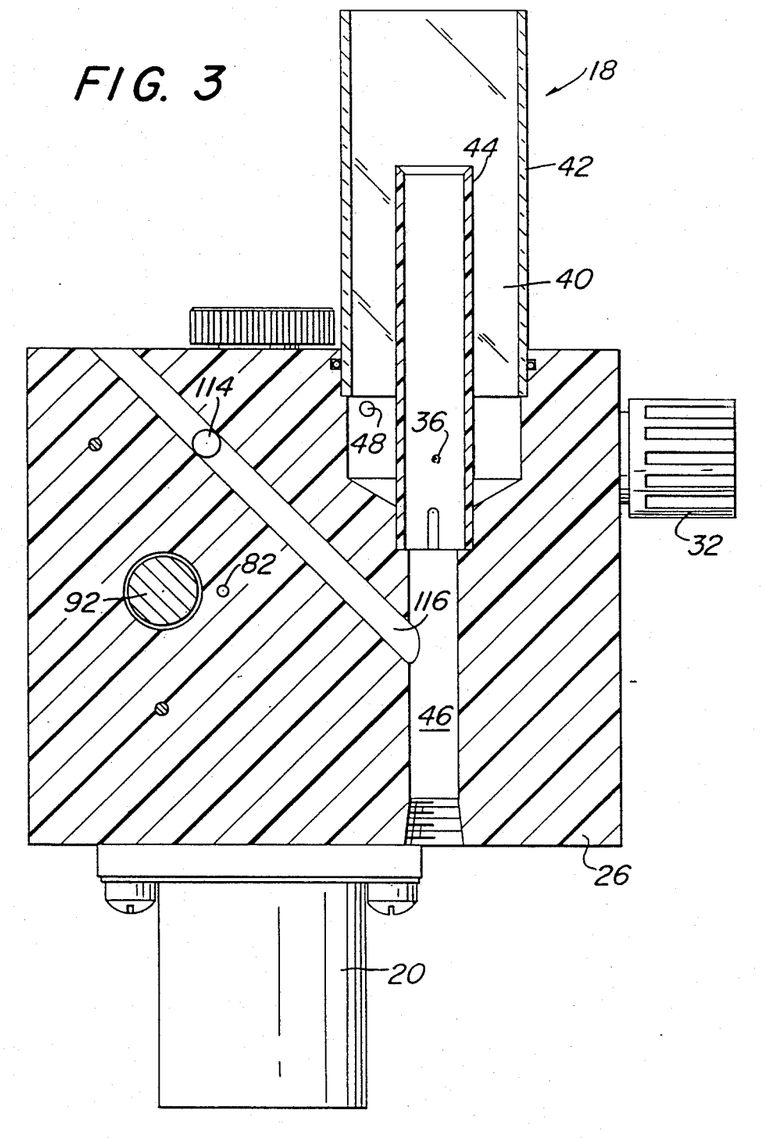
FIG. 3 is a cross-sectional view of the working fluid sampler system, as contemplated by the present invention, taken along line 3—3 in FIG. 2.

As shown in FIG. 3, second passageway 36 enters an annular chamber 40 within flow block 26 at the base of the constant level box 18. The constant level box 18 comprises an outer cylindrical housing 42 which projects vertically from the upper surface of the flow block 26 and defines the remainder of annular chamber 40. An internal tube 44 having a smaller diameter than that of housing 42 is also fixed at the base of the annular chamber 40 and projects from the base concentrically with housing 42. The projection of the cylindrical housing 42 is greater than that of of the internal tube 44. Tube 44 is connected at its base with exhaust passageway 46 to provide an outlet for the unused portion of the flow entering the constant level box 18 so as to return this flow back into the working fluid stream.

The amount of flow entering the annular chamber 40 through second passageway 36 is preferably regulated to be greater than the amount of flow which will pass through the outlet of the box 18 which is defined by first sample passageway 48. The fluid in chamber 40 builds to a level which fills the volume defined by the cylindrical housing 42 less tube 44. A pressure head is created by the level of fluid above the outlet 48 of the annular chamber 40. The maximum head created is defined by the height of the upper rim of the internal tube 44 above the outlet 48. The fluid level upon reaching the top of internal tube 44 will flow over the upper rim and be exhausted through exhaust passageway 46. Thus, a constant pressure is maintained on the fluid passing through the first sample passageway 48 and this pressure is fixed by the height of internal tube 44 within chamber 40.

Figure 4:
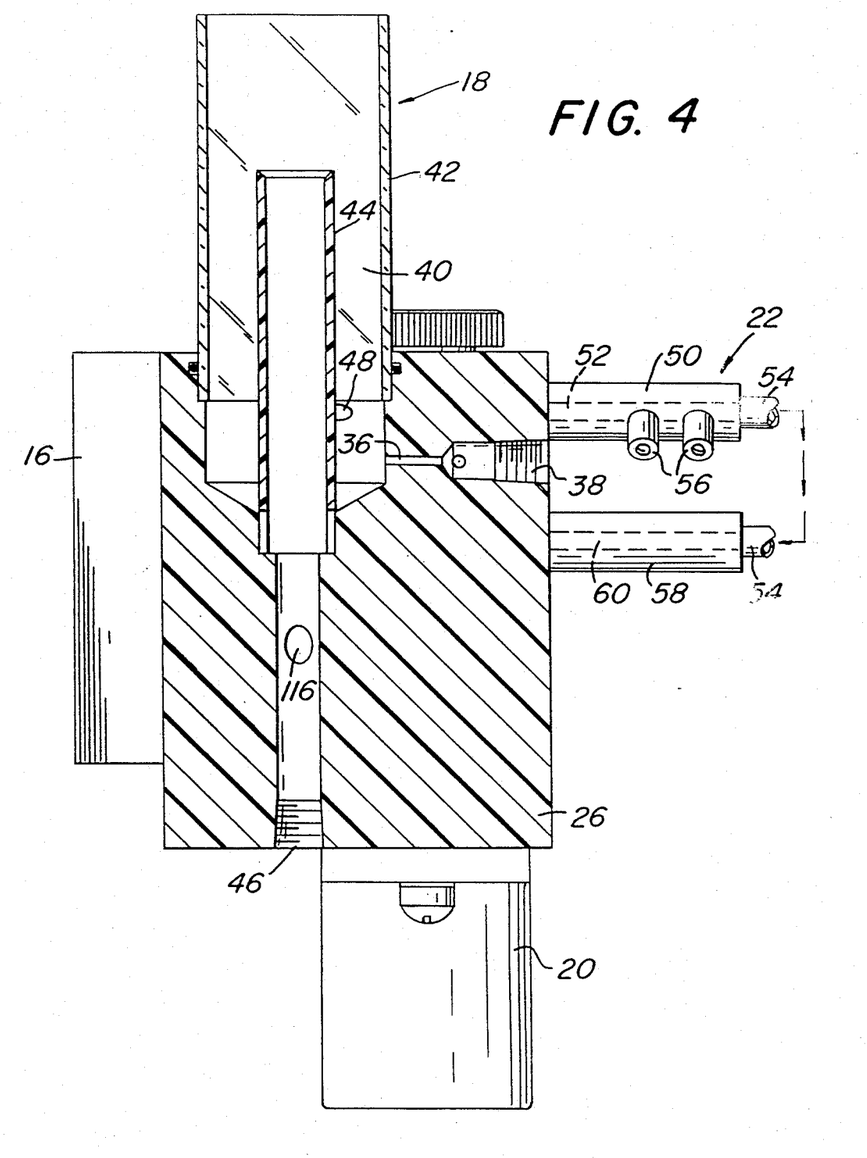
FIG. 4 is a cross-sectional view of the working fluid sampler system, as contemplated by the present invention, taken along line 4—4 in FIG. 2.

As shown in FIG. 4, the first sample passageway 48 directs the flow from the annular chamber 40 through the flow block 26 to the flow delay line 22. Flow delay line 22 includes a first delay fitting 50 attached at one end to the flow block 26 and having an internal channel 52 which communicates between the first sample passageway 48 and a delay line 54. Communicating with the first delay fitting 52 is means 56 to add reagent to the flow passing through internal channel 52. Typically, the reagent will be added at an extremely low flow rate. The delay line 54 may be of any size or shape as required for proper mixing of the reagent with the sample flow. The time required for the reagent to properly condition the sample for analyzation determines this length. Delay line 54 is attached at its outlet to a second delay fitting 58 having an internal channel 60. Internal channel 60 communicates with a second sample passageway 62 (shown in FIGS. 2 and 10) which communicates with the backflush mechanism 20 mounted within flow block 26.

Figure 5:
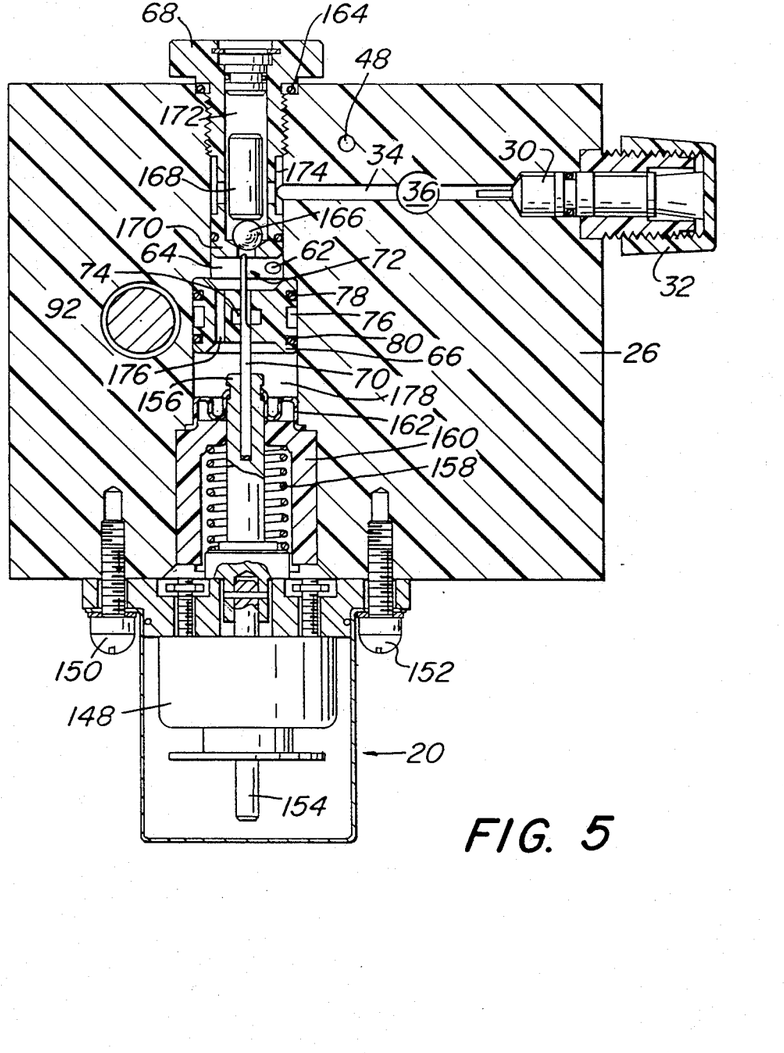
FIG. 5 is a cross-sectional view of the working fluid sampler system, as contemplated by the present invention, taken along line 5—5 in FIG. 2.
Figure 11:
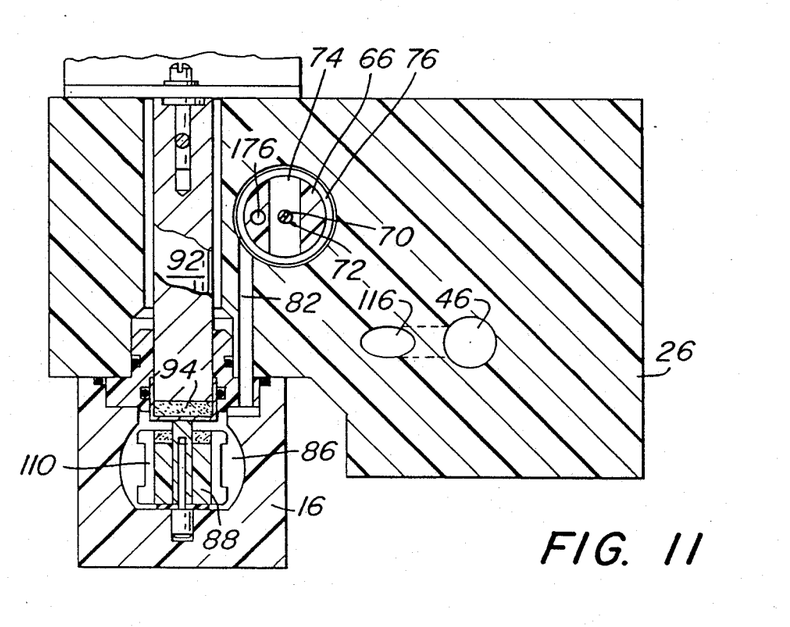
FIG. 11 is a cross-sectional view of the working fluid sample system, as contemplated by the present invention, taken along line 11—11 in FIG. 6.

A backflush chamber 64 is formed by the internally mounted structure of backflush mechanism 20 positioned within a stepped bore through the flow block 26. As can be seen in FIGS. 5, 10 and 11, the chamber 64 which is defined by the walls of the bore within the flow block 26, orifice 66 and check valve retainer 68. The sample flows into the backflush chamber 64 through the second sample passageway 62 and is directed into the orifice 66. A central bore is defined through orifice 66 in which a plunger rod 70 is inserted. Plunger rod 70 on its upper end includes a flat 72 which permits the flow to pass into the central bore of the orifice 66 then through orifice opening 74. Orifice opening 74 is a transverse slot through orifice 66 which communicates with a circumferential channel 76 defined by the orifice 66 and the walls of the bore in flow block 26. Circumferential channel 76 is sealed by O-rings 78 and 80. The flow entering the orifice opening 74 passes through circumferential channel 76 and into a third sample passageway 82 which directs the flow into the probe block 16 (See FIG. 11).

The operation of the backflush mechanism 20 has been described only with respect to its function in directing the flow from the flow delay line 22 into the probe block 16. The operation of the backflush mechanism 20 for cleansing the internal passageways of the flow block 26 will be described later in this text.

Figure 6:
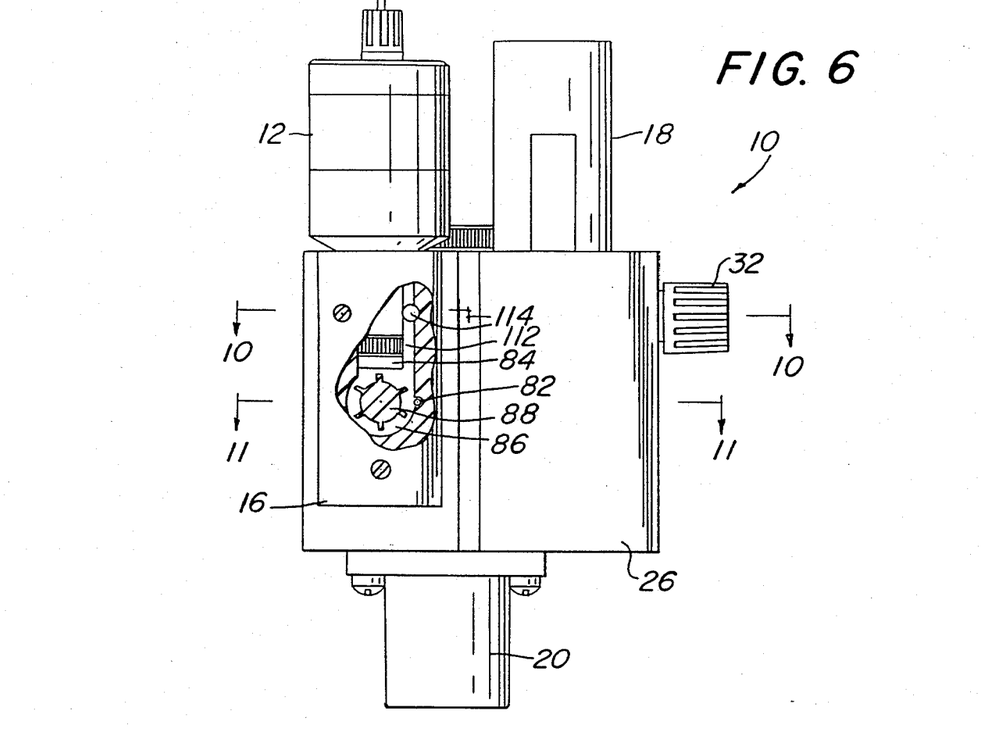
FIG. 6 is a side elevation of the residual analyzer assembly shown in FIGS. 1 and 2 having internal structure exposed.
Figure 7:
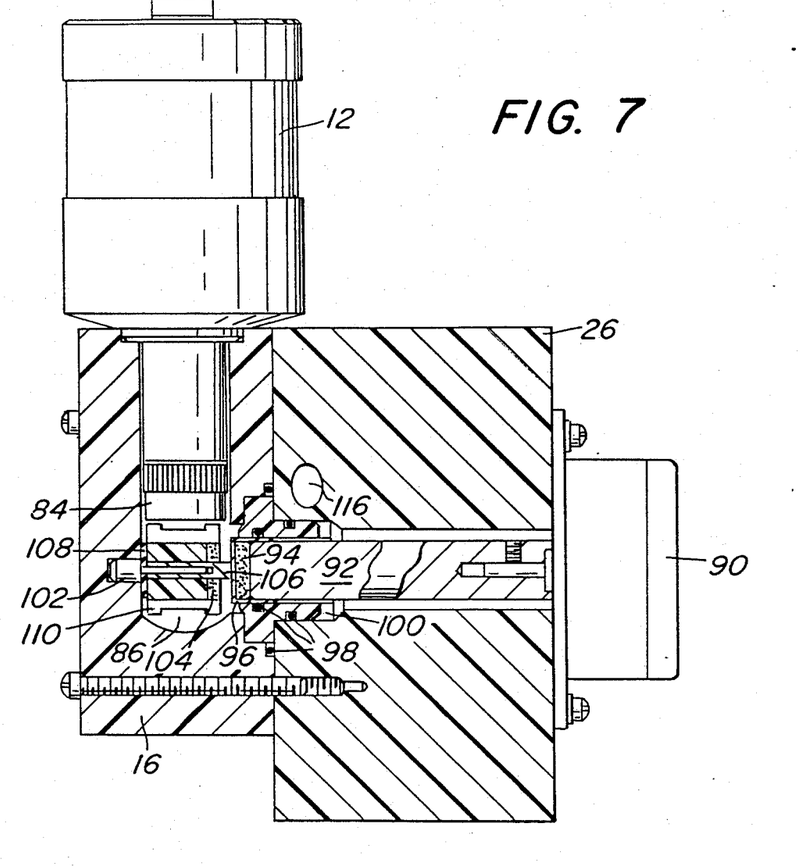
FIG. 7 is a cross-sectional view of the working fluid sampler system, as contemplated by the present invention, taken along line 7—7 in FIG. 2.

As shown in FIGS. 6 and 7, probe 12 is supported on probe block 16 which is attached to and communicates with the internal passageways of flow block 26. The end face 84 of the probe 12 is positioned adjacent an impeller chamber 86 within the probe block 16. Mounted for rotation within the chamber 86 is an impeller 88 adapted to provide a constant sample velocity adjacent the end face 84 of the probe 12. As shown in detail in FIGS. 7 and 11, the impeller mechanism 24 includes a motor 90 which rotates a coupling 92 and a permanent magnet 94 supported on the end of the coupling 92 adjacent impeller chamber 86. Magnet 94 is preferably sealed with respect to the working fluid within the impeller chamber 86 by means of a cup 96. The motor 90 and coupling 92 are sealed by a series of O-rings 98 positioned around a flange 100. Impeller 88 is mounted on a fixed shaft 102 which projects into the impeller chamber 86 from the wall opposite of the position of the permanent magnet 94. The impeller 88 is free to rotate on shaft 102 and includes a permanent magnet 104 which is spaced from coupling magnet 94 by means of a projecting portion of impeller shaft 106.

A grit material is contemplated to be utilized within the impeller chamber 86 for continuous cleaning of the probe end face 84 and chamber 86. A bushing, preferably of a Teflon material, may be provided adjacent the impeller 88 and the wall of the impeller chamber 86 in which the fixed shaft 102 is mounted. The bushing 108 will prevent grit from impairing the rotation of the impeller 88 or causing the impeller 88 to separate from its magnetic coupling with magnet 94. The impeller shaft 106 and the protective cup 96 are preferably made of a hastelloy material to prevent corrosion due to the reagents as typically utilized in such systems, such as sulfuric or acetic acids or salts.

Figure 8:
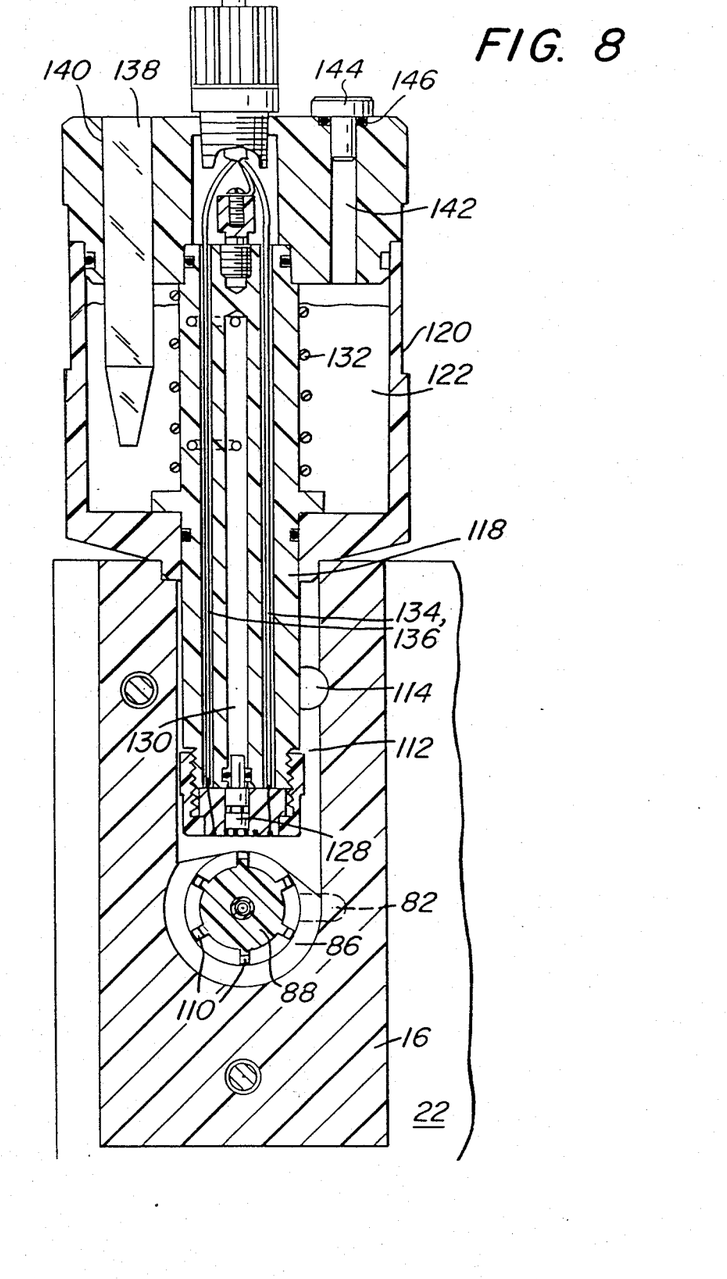
FIG. 8 is a cross-sectional view of a residual analyzer probe, as contemplated by the present invention, taken along line 8—8 in FIG. 2.

As also shown in FIGS. 6 and 8, the impeller 88 is free to rotate directly adjacent to the end face 84 of the probe 12. The impeller blades 110 are preferably designed, along with the impeller chamber 86, to create a constant flow velocity directly adjacent the end face 84 of the probe 12. The impeller 88 as shown includes projecting flanges adjacent to the ends of the impeller blades 110 to assist in directing the grit material within the chamber 86 to clean the end face 84 of the probe 12. The grit material is continuously rotated within the impeller chamber 86 due to the action of the impeller 88 and is preferably not exhausted from the chamber 86 with the normal flow of the working fluid sample.

The impeller chamber 86 includes an upwardly extending channel 112 which is positioned adjacent the portion of the probe 12 projecting into probe block 16. An outlet passageway 114 from channel 112 is located above the inlet of third sample passageway 82 into chamber 86 so that the pressure created by the moving fluid assists in the exhaust of the flow from chamber 86 without causing the grit material to flow along with the sample. As shown in FIG. 10, the outlet passageway 114 directs the sample exhaust from chamber 86 into an angled exhaust shaft 116 which communicates with exhaust passageway 46. The pressure head required to raise the level of the fluid sample to the position of outlet passageway 114 is created by the head of constant level box 18.

FIG. 8 shows in cross-section a preferred embodiment of the probe 12 as contemplated for use within the working fluid sampler system 14 or which may be adapted for use with any type working fluid system as desired. The end face 84 of the probe 12 is preferably in the form of a cap and is attached by means of a threaded coupling to a shaft 118 which is shown positioned within the probe block 16 adjacent channel 112. The probe shaft 118 is connected at its opposite end to a probe body 120 which includes an internal chamber 122.

Figure 9:
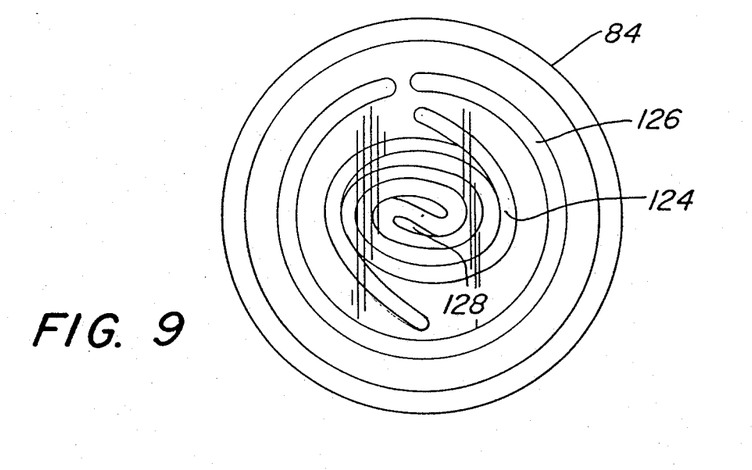
FIG. 9 is a plan view of the end face of the cap portion of a residual analyzer probe, as contemplated by the present invention.

As can be seen in FIG. 9, the end face 84 of the probe 12 includes a first or working electrode 124 and a second or counter electrode 126. The working electrode is formed in a double spiral helix at the center of end face 84. The counter electrode 126 is positioned directly adjacent the working electrode 124 and forms an annular ring or circle surrounding the the working electrode 124. It is preferred that both of these electrodes 124, 126 be made of a platinum material. However, the electrode materials may vary depending on the type of analyzation that is to be preformed.

The proximity of the counter electrode 126 with respect to the working electrode 124 is desired to be close so as to reduce the ohmic drop between the two during operation. A flexible membrane 128 may be positioned directly behind the working electrode 124 and end face 84. The membrane 128, which is preferably made of a hydrophilic polypropylene material, is protected by the working electrode 124 during operation such that the grit which is rotated by impeller 88 does not damage the thin membrane material. Additionally, membrane 128 is connected, via a channel 130 within shaft 118, to internal chamber 122. Both the channel 130 and the chamber 122 are filled with an electrolytic solution. A third or reference electrode 132 is provided within the electrolytic solution. The reference electrode 132 is preferably formed in a coil and made of silver.

Figure 12:
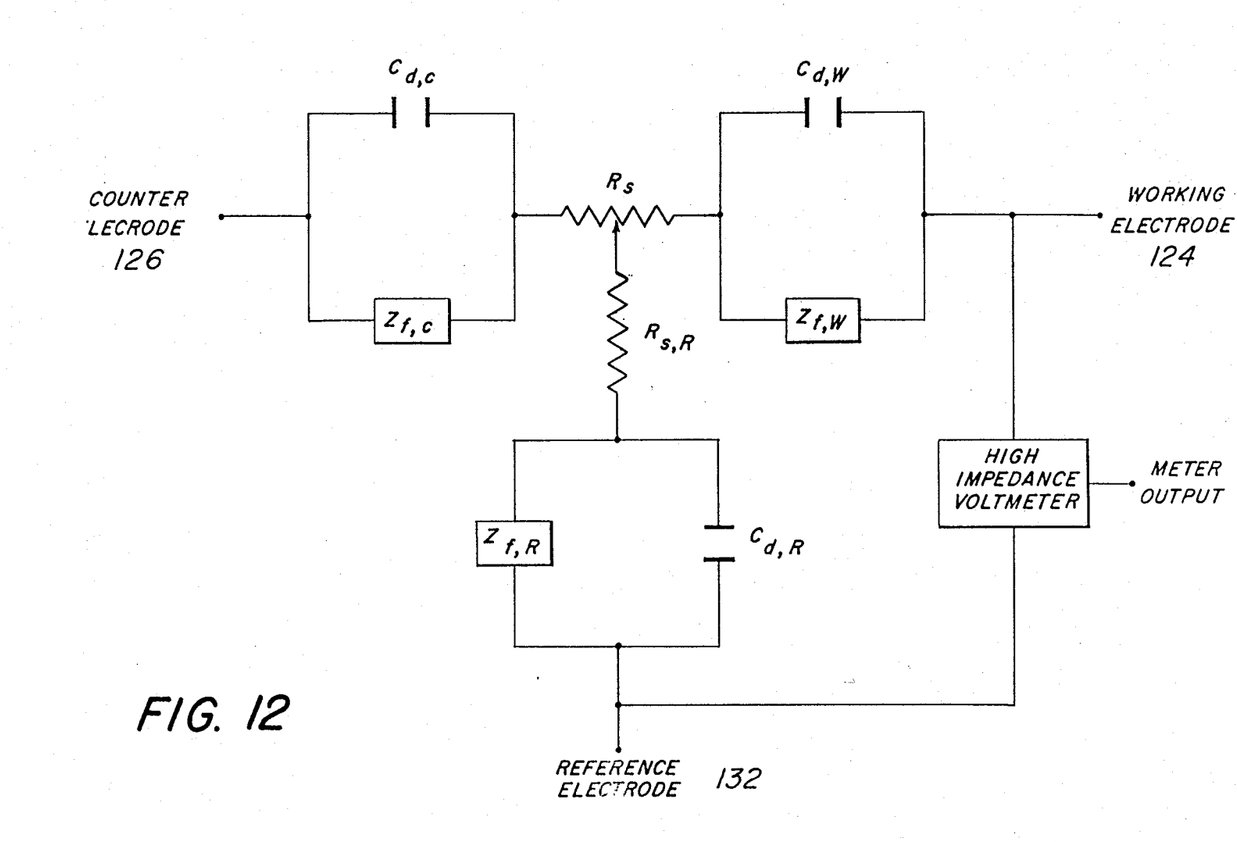
FIG. 12 is a simple representation of a three electrode potentiostat circuit.

As shown in FIG. 12, the three electrode configuration is preferably operated utilizing a potentiostat circuit of the type employed in a variety of electrochemical measurements and laboratory instrumentation. The potentiostat circuit of the present invention, preferably, employs an instrument to read the potential between the working electrode 124 and the reference electrode 132 while allowing current only to flow between the counter electrode 126 and the working electrode 124. The potential may be controlled in one instance and the current measured or the opposite may be performed as desired. Virtually zero current flows through the reference electrode 132; thus, rendering a major portion of the ohmic resistance and impedances between the counter electrode 126 and reference electrode 132 insignificant. Since the reference electrode 132 sees only the potential difference between itself and the working electrode 124, only the impedance between the tip of the reference electrode 132 and the working electrode 124 manifest itself in the measurement. Thus, a major portion of the bulk ohmic resistance and the interfacial impedances of the counter electrode 126 and reference electrode 132 are rendered insignificant. The impedance between membrane 128 and the working electrode 124 is also minimized by the placement of the membrane 128 directly behind working electrode 124 and probe end face 84.

The three electrode configuration and its circuitry maintains a fixed electrochemical potential on the working electrode 124 by minimizing the ohmic resistance and impedances between the counter electrode 126 and working electrode 124 and the reference electrode 132 and working electrode 124. The fixed working electrode potential results in greater selectivity, stability, and a near zero cell current at zero concentration. This results in the probe 12 having the ability to measure low residuals and eliminates the need for a periodic zero calibration adjustment. Additionally, since the end face 84 of probe 12 is attached to the probe shaft 118 by means of a threaded engagement, replacement of the electrodes 124, 126 and/or the membrane 128 may be made easily by unscrewing the end face cap 84 and unplugging the electrode assembly from the electrical connection within shaft 118. The electrical connection with electrodes 124, 126 are made through the shaft 118 via wires 134 and 136.

The probe 12 on its upper end may also contain a viewing cap 138 which comprises an insert into bore 140. The unexposed end of the view plug 138, which is preferably made of a translucent material, projects into the electrolytic solution within internal chamber 122; such that when the electrolyte is at its proper level within the chamber 122, the view plug 138 will appear dark. However, if the level of electrolytic solution within the chamber 122 is below the end of the view plug 138, the visible end of the plug 138 will appear light or clear. On the radially opposite side of the top of the probe 12 is a second bore 142 which retains a plug 144 having a porous vent within its interior. Plug 144 is inserted into bore 142 and is sealed by means of an O-ring 146. Plug 144 preferably includes an internal core of a porous material to permit pressure relief from the internal chamber 122.

Returning now to FIG. 5 which shows the structure of the back flush mechanism 20, a solenoid 148 is shown attached to the flow block 26 via screws 150 and 152. A plunger 154, operated by the solenoid and attached to a piston 156, is biased by a spring 158 so that the plunger 154 in the unactuated position is in its downward or relatively low position. The piston 156 is slideably maintained within a fixed housing 160 with the spring 158 biasing the piston downward with respect to the housing 160. The housing 160 is sealed from exposure to the working fluid sample by gasket 162. Projecting from the piston 156 is plunger rod 70 which extends through the orifice 66 and into chamber 64 as previously described.

The upper or projecting end of the plunger rod 70 extends to a position adjacent the check valve retainer 68. Check valve retainer 68 is inserted through the top of the flow block 26 and is engaged within the upper end of the bore by means of a screw thread. An O-ring 164 may be provided so as to further seal the enclosure. Retainer 68 includes a ball check 166, a sliding weight 168 and an internal valve seat 170 all retained within a chamber 172. In its normal or rest position the ball check 160 is seated on valve seat 170, which is open at its lower end into back flush chamber 64, with the sliding weight 168 resting on the check valve 168 so as to further seal the chamber 172 from chamber 64.

Chamber 172 of the retainer 68 includes a number of orifices 174 which are in communication with first passageway 34. During normal operation, the sample fluid flow from the flow delay line 122 moves through the second sample passageway 62 into the backflush chamber 64. The pressure of the sample flow entering from the second sample passageway 62 is less than the full flow moving through the first passageway 34 into the internal chamber 172 of the check valve retainer 68 due to the structure of the constant level box 18. The first passageway 34 is at the same pressure as the flow entering the flow block 26 whereas the pressure through the second sample passageway 62 is dependent upon the head created by the constant level box 18. This pressure differential further maintains the seal of the ball check 166 within the valve seat 170.

Periodically, the internal passageways of the flow block 26 are desired to be cleaned to remove any buildup of materials which may have formed. The backflush mechanism 20 is energized by the solenoid 148 moving its plunger 150, the piston 156 and rod 70 in an upward direction. The seal created by the ball check 166 is released from the valve seat 170 by the end of rod 70 and flow is permitted to enter backflush chamber 64 through valve seat 170. Additionally, flat 72 on the plunger rod 70 is moved to a position such that the orifice opening 74 is sealed with respect to the backflush chamber 64. Therefore, the flow into the third sample passageway 84 and the impeller chamber 86 is prevented during backflush. Due to the greater flow pressure within the first passageway 34 over that from the flow in the second sample passageway 62, the first passageway 34 now controls the direction of flow through the flow block 26. This flow moves through second sample passageway 62 opposite the normal sample flow direction, through the flow delay line 22 and first sample passageway 48, back into the constant level box 18. Since the third sample passageway 82 is sealed with respect to the backflush chamber 64, the grit and other materials which are retained within the impeller chamber 86 are not removed during backflush. The materials which are backflushed through the system are moved into the constant level box 18 and are exhausted through the exhaust passageway 46. Upon deenergization of the solenoid 148, the plunger 154, piston 156 and rod 70 are moved downward due to the action of spring 158 and the ball check 166 is returned to the valve seat 170 so as to resume normal flow of the sample into impeller chamber 86.

As also can be seen in FIG. 5, orifice 66 includes an axial bore 176 which permits a portion of the flow entering backflush chamber 64 to move into lower chamber 178 adjacent gasket 162. During activation of solenoid 148, the piston 156 moves rapidly into chamber 178 and forces flow back through axial bore 176 to further causes release of ball check 166 from valve seat 170. The back pressure in lower chamber 178 also helps retain orifice 66 in its position within the bore in flow block 26 during this backflush.

In typical operation, the constant level box provides a flow rate substantially less than the full flow entering the flow block 26. The quantity of conditioning reagent required in the system, therefore, is greatly reduced. However, due to the reduction in the sample flow through the assembly 10, a build up of organic matter could cause a residual demand and affect the accuracy of the residual measurement or completely block flow. Therefore, to minimize this possibility the system, either automatically or manually, periodically energizes the solenoid 148 which raises the plunger rod 70 to open the backflush. The movement of the plunger rod 70 also removes any material which has been entrained within the orifice 66.

The probe 12 so contemplated by the present invention provides a near true zero reading and a stable zero calibration. The working fluid sampler system 14 is combined with the contemplated probe 12 to result in a substantial cost savings in reagent usage and an increased sensitivity, especially for low residual measurement. The backflush mechanism which may be made substantially automatic to minimize operator maintenance and permit utilization in cooling and waste water type systems where electrode fouling would be frequent.

The present invention may be embodied in other specific forms without departing from the spirit or essential attributes thereof and, accordingly, reference should be made to the appended claims, rather than to the foregoing specification, as indicating the scope of the invention.

I claim:

1. A probe for residual analyzation of working fluid, the probe comprising: three electrodes including a first electrode having a double spiral configuration, a second electrode forming an outer ring closely adjacent the first electrode, the first and second electrodes adapted for direct contact with the working fluid and a third electrode positioned within an electrolytic solution within an internal chamber in a probe body and a membrane immediately adjacent the first electrode, the membrane in communication with the third electrode through the electrolytic solution.

2. A probe as claimed in claim 1 further comprising means for operating the three electrodes in a potentiostat circuit with the first electrode acting as a working electrode, the second electrode acting as a counter electrode, and the third electrode acting as a reference electrode, a potential being maintained between the working and reference electrodes while current being permitted to flow only between the counter and working electrodes.

3. A probe as claimed in claim 1 wherein the first and second electrodes are made of a platinum.

4. A probe as claimed in claim 1 wherein the third electrode is made of a silver and is maintained within a potassium chloride electrolytic solution.

5. A probe as claimed in claim 1 wherein the membrane is a hydrophilic polypropylene.

6. A probe as claimed in claim 1 further comprising means to determine the level of electrolytic solution within the internal chamber of the probe.

7. A probe as claimed in claim 1 further comprising means to vent the internal chamber of the probe body.

8. A residual analyzer assembly comprising: an amperometric probe including two exposed electrodes, one comprising a working electrode having a double spiral configuration and the other comprising a counter electrode forming a ring around the double spiral configuration, a chamber within the probe having an electrolytic solution therein, means defining a reference junction immediately adjacent the working and counter electrodes, and a reference electrode positioned within the chamber of said probe.

9. A residual analyzer assembly as claimed in claim 8 further comprising a working fluid sampler system having means for receiving a flow of working fluid and withdrawing a sample therefrom, means for maintaining a constant pressure on the sample, means for adding reagent to the sample, means for controlling the reagent reaction time with the sample, means for directing the sample into an impeller chamber and impeller means adapt to maintain a constant flow velocity adjacent the exposed electrodes of the probe.

10. A residual analyzer assembly as claimed in claim 9 further comprising means for periodically backflushing the working fluid through the reagent reaction control means, the reagent addition means and the fluid sampling means, opposite the normal sample flow direction.

11. A residual analyzer assembly as claimed in claim 10 further comprising means for applying a potential between one of the exposed electrodes and the third electrode and further adapted for permitting current flow only between the two exposed electrodes.

12. A residual analyzer assembly as claimed in claim 11 wherein the applying means operates in conjunction with a potentiostat circuit.

13. A residual analyzer assembly as claimed in claim 10 further comprising means to maintain a grit material within the impeller chamber for cleaning of the exposed electrodes of the probe.

14. A working fluid sampler assembly adapted for residual analyzation of a working fluid, the assembly comprising: means for receiving a flow of working fluid, means for sampling the flow of working fluid, means for maintaining a constant pressure on the sample, means for adding reagent to the sample and further adapted to control the time of reaction of the reagent with the sample, means for directing the sample from the reagent addition means to an impeller means, said impeller means adapted to maintain a constant flow velocity adjacent a residual analyzer probe and means for periodically causing a backflush of the working fluid through the directing means, the reagent addition means and the sampling means, but not the impeller means, opposite the normal sample flow direction.

15. A working fluid sample assembly as claimed in claim 14 further comprising an amperometric probe having a stable zero calibration, the probe being positioned adjacent the impeller means.

16. A working fluid sample assemby as claimed in claim 15 wherein the probe comprises two exposed electrodes and a reference electrode within an electrolytic solution behind a membrane.

17. A working fluid sample assembly as claimed in claim 16 wherein the two exposed electrodes further comprise a double spiral wound working electrode and a substantially circular counter electrode surrounding the working electrode.

18. A working fluid sample assembly as claimed in claim 17 wherein the membrane is positioned behind the working electrode.

19. A working fluid sample assembly as claimed in claim 18 wherein the working and counter electrode are supported on a detachable cap.

20. A working fluid sample assembly as claimed in claim 19 wherein the membrane is supported on the probe behind the detachable cap.

* * * * *